July 22, 1975 TAKESHI YOICHI YONEMOTO Plant Pat. 3,746
CARNATION PLANT
Filed July 3, 1974
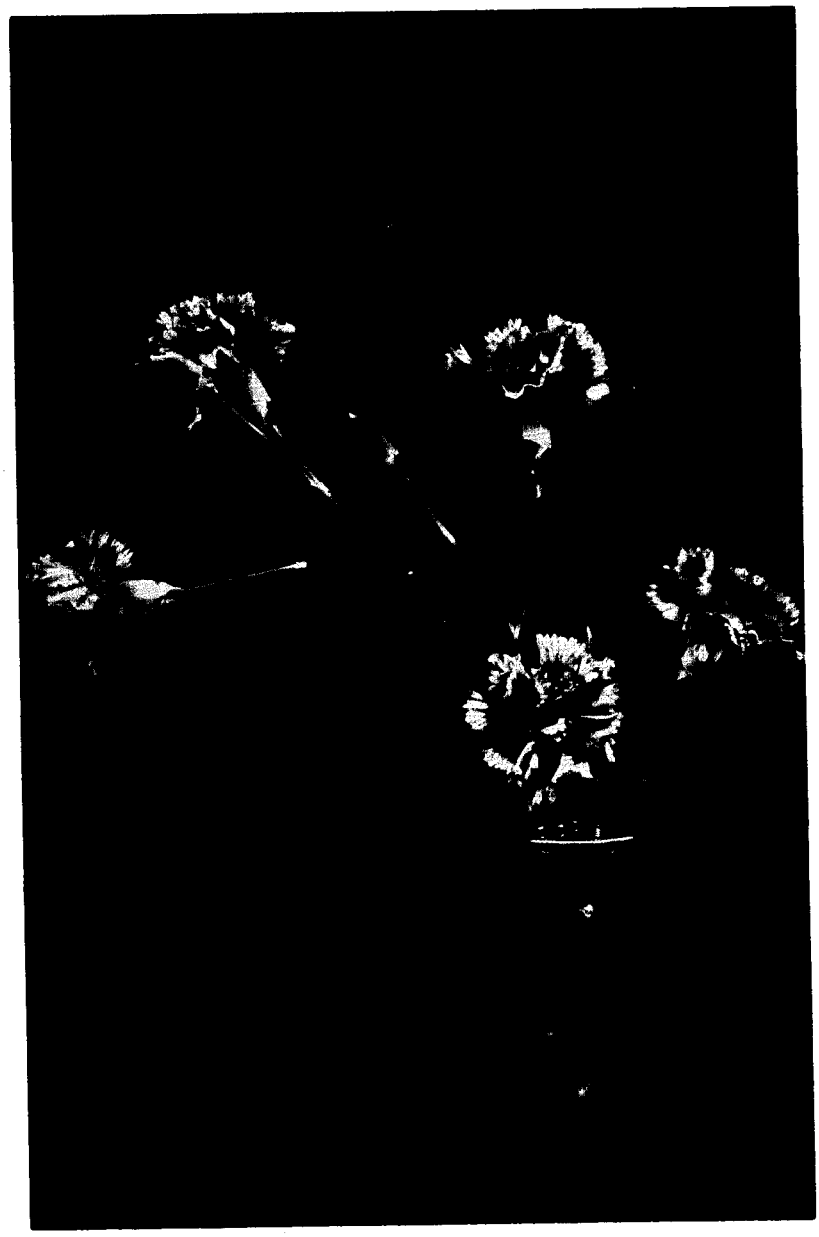

United States Patent

Plant Pat. 3,746
Patented July 22, 1975

3,746
CARNATION PLANT

Takeshi Yoichi Yonemoto, 1328 Henderson Ave., Santa Clara, Calif. 95051

Filed July 3, 1974, Ser. No. 485,384
Int. Cl. A01h 5/00
U.S. Cl. Plt.—70 1 Claim

ABSTRACT OF THE DISCLOSURE

A new variety of carnation plant originated as a sport of the variety Petite Purple (unpatented) which in turn is a sport of Exquisite Select (unpatented), the new sport being particularly distinguished by the purple and white coloring of its "miniature" sized blossoms and its relatively long lasting quality as a cut flower.

*Background of the New Plant*

This new variety of carnation was discovered by me in 1971 among a group of plants of the variety Petite Purple (unpatented) being grown in my greenhouse at Santa Clara, Calif., with the object of producing miniature carnations having a new purple coloration of its blossoms and a vigorous growth habit for the year around production of attractive cut flowers.

This new sport exhibited a different purple coloring than its parent and the end portions of its outer flower petals were heavily streaked with white bands which stopped just short of the petal end margin, which remained purple but of a somewhat lighter color. Because of this difference of coloration over that of the parent variety, this new variety appeared to have commercial merit and accordingly asexual propagation of the plant under my direction was begun to test the plant for stability. Continued progagation from generation to generation by cuttings has demonstrated that this new plant has retained the structure and growth characteristics of its parent and that the new flower coloring is firmly fixed and holds true from generation to generation. Propagation of this new variety on a commercial scale is now being carried on by means of cuttings at Santa Clara, Calif.

*Description of the Drawing*

My new variety of carnation is illustrated by the accompanying drawing which shows, in full color, buds and fully opened flowers the coloration of which is reproduced as nearly true as it is reasonably possible to do by conventional photographic procedures.

*Description of the New Plant*

The following is a description of my new variety of carnation plant with the color designations according to the R.H.S. Colour Chart of The Royal Horticultural Society of London, England.

THE PLANT

Origin: Sport.
Parentage: Petite Purple (unpatented).
Classification:
- Botanic: Dianthus caryophyllus.
- Commercial: Greenhouse carnation for cut flower production.

Form: Bush.
Height: 2 to 3 feet.
Growth: Vigorous and upright with strong stems.
Growth Rate: Four months to blooming.
Foliage: Average abundance with 9 smooth textured leaves per stem.
- Texture: Smooth.

THE BUD

Form: Before opening, long ovoid with white tipped pointed apex.
Size: Small.
- Diameter—about ⅜ inch.
- Length—¾ inch.

Sepals: Erect and linear in shape with acute apex having a white margin.
Aspect: Smooth.
Opening Rate: Six days.
Splitting: None.
Peduncle: 2 to 3 inches long.

THE FLOWER

Blooming Habit: Continuously and profusely the year around.
Size: Miniature.
- Diameter—1½ inches.
- Depth—¾ inch.

Borne: In clusters.
Shape: Cup shaped with high center.
Petalage: Number—29 to 31.
- Form: Fan shaped with very distinctly serrated margin.
- Color: Outer portions—Purple R.H.S. 74B. Inner portions—Purple R.H.S. 61A. Reverse side—Lighter shades of purple.
  - Outer portions of outer petals are streaked with lengthwise bands of almost white color which extend inwardly about ⅓ of the petal length.
- Texture: Soft.
- Appearance: Velvety.

Fragrance: Slight.
Lasting Quality: 2½ weeks as cut flower.

REPRODUCTIVE ORGANS

Stamens:
- Anthers: 12 in number, each ⅛ inch long.
- Filaments: Emerge from base of ovary. Length—¾ inch. Color—Light Green.
- Pollen: Color—Yellow.

Pistils: Number—2. Length—½ inch.
- Stigmas: Color—Purple.

Ovaries: Oblong or upright egg shaped, ⅝ x ⅜ inch in size. Color—Green.

I claim:

1. A new and distinctive variety of carnation plant, substantially as herein shown and described, characterized by the purple and white coloration of the flower petals.

No references cited.

ROBERT E. BAGWILL, Primary Examiner